United States Patent [19]

Conkle et al.

[11] 3,951,137

[45] Apr. 20, 1976

[54] REBREATHING SYSTEM

[75] Inventors: James P. Conkle; Marvin A. Rosenbusch; Doyle D. White, all of San Antonio, Tex.

[73] Assignee: The United States of America as represented by the Secretary of the Air Force, Washington, D.C.

[22] Filed: Nov. 20, 1974

[21] Appl. No.: 525,711

[52] U.S. Cl............................ 128/2.08; 128/145.8; 128/DIG. 17; 128/DIG. 29
[51] Int. Cl.² ..................... A61B 5/08; A61M 16/00
[58] Field of Search............... 128/2.08, 2.07, 145.5, 128/145.6, 145.8, 142.2, DIG. 17, DIG. 29

[56] References Cited
UNITED STATES PATENTS

| | | | |
|---|---|---|---|
| 3,033,195 | 5/1962 | Gilroy et al. | 128/145.8 |
| 3,283,754 | 11/1966 | Goodner | 128/145.8 |
| 3,307,542 | 3/1967 | Andreason | 128/145.8 |
| 3,695,263 | 10/1972 | Kipling | 128/145.6 |
| 3,729,000 | 4/1973 | Bell | 128/145.6 |
| 3,730,180 | 5/1973 | Davison | 128/145.6 |
| 3,769,967 | 11/1973 | Jones et al. | 128/2.08 |
| 3,850,170 | 11/1974 | Cox | 128/145.8 |

OTHER PUBLICATIONS

Mitamura, "Optimally Controlled Respirator," IEEE Trans. on Bio–Med. Eng., Vol. 18, No. 5, Sept. 1971, pp. 330–338.

*Primary Examiner*—Robert W. Michell
*Assistant Examiner*—Lee S. Cohen
*Attorney, Agent, or Firm*—Joseph E. Rusz; Jacob N. Erlich

[57] ABSTRACT

A constant volume rebreathing system when utilized in conjunction with an external air source, such as man. The rebreathing system forms a completely closed system between man and the environment. There is a stainless steel bellows within the system which in conjunction with ancillary equipment controls the differential pressure between man's lung and the bellows. A pressure transducer senses any pressure change and in accordance therewith alters the volume of the bellows, thereby assisting man's use of the rebreathing system. In addition analyzers are located within the system to monitor the various gases present.

11 Claims, 5 Drawing Figures

REBREATHING SYSTEM

STATEMENT OF GOVERNMENT INTEREST

The invention described herein may be manufactured and used by or for the Government for governmental purposes without the payment of any royalty thereon.

BACKGROUND OF THE INVENTION

This invention relates generally to rebreathing systems, and, more particularly, to a constant volume rebreathing system which provides a completely closed breathing system between man and the external environment. Such a system is especially useful for the collection of expired air samples from humans.

It is essential in the field of medicine as well as the space program to provide a rebreathing system which is capable of collecting non-contaminated expired air samples. Such samples, with subsequent analysis, can provide information in the following areas of interest:

1. Forensic medicine;
2. Respiratory compounds as indicators of metabolic disease and the disease state;
3. Determination of toxin in toxic exposure;
4. Determination of the degree of stress;
5. Normal compounds associated with man as related to diet;
6. Drugs and drug metabolism; and
7. The inhalation study of particles and gaseous compounds.

Heretofore, the techniques and designs which made breath by breath analysis of a subject possible was in the form of a water spirometer. In such a system no controls are included to improve data results, while in many instances leakage from ambient air causes data to misrepresent components in the subject's expired air. Furthermore, the water spirometer of the past has the following distinct disadvantages:

1. It has a water interface which may absorb the components of interest;
2. The breath by breath energy expended by the subject to operate the spirometer causes early fatigue in the subject before sufficient data can be taken;
3. The dynamic range of the water spirometer requires the subject to remain in a fixed position; and
4. The spirometer cannot be used as a respiratory simulator.

It is therefore clearly evident that a great many problems exist in the area of breath analysis. There is a complete lack of functional equipment in a field which is rapidly expanding.

SUMMARY OF THE INVENTION

The instant invention sets forth a constant volume rebreathing system which overcomes the problems encountered in the past as set forth in detail hereinabove.

This invention provides a completely closed breathing system between man and the external environment. The incorporation of flexible metal bellows eliminates the diffusable barriers found in other systems such as polymeric organic materials and water, thereby eliminating gaseous diffusion. In addition, the utilization of a pressure transducer, used to drive a stepping motor incorporated as a servo system amplifying the action of the subjects respiratory effect, reduces the fatigue usually associated with rebreathing systems of the past.

The internal system of this invention exposed to the environment of man consists of only inert materials such as stainless steel, organic polymeric materials of inert qualities with low surface exposure such as seals and gaskets, Barlyme, and the respiratory system of the subject. Furthermore, the instant rebreathing system offers the capability of being used as a respiratory simulator with only minor modifications.

The constant volume rebreathing apparatus of the instant invention is made of a stainless steel bellows connected to ancillary systems in order to obtain a working constant volume rebreathing system when the human lung/diaphragm is incorporated in the system.

The invention provides for control of the volume in the bellows portion of the system. A circuit to control air volume utilizes a translator motor control and a Saginaw Ball Screw Drive to open and close the stainless steel bellows. The bellows is connected to a breathing valve for a human subject. Signal input for the control system is furnished by a highly sensitive pressure transducer through an inverting and non-inverting amplifier to the translator.

The rebreathing system controls the differential pressure between the human subject's lungs and the stainless steel bellows. As the subject inspires, the pressure transducer senses the pressure change, presents the signal through the control amplifier to the translator which drives the motor control for the bellows decreasing the volume of the bellows, conversely as the subject expires the motor opens the bellows. A constant volume in the lung-rebreathing system is therefore maintained. A differential pressure of +2 mm to −1 mm during normal respiration is produced by the instant invention.

A two-way breathing valve is incorporated into the system. This valve allows exhaled air to be delivered to the bellows. Inhaled air is drawn from the bellows through a Barlyme Canister through the valve and into the lungs. Incorporated into the system is a solenoid operated over-pressure valve. At 6 mm Hg, the over-pressure valve opens the bellows to ambient air, thereby providing protection to the subject in the event of a system malfunction producing lower or higher pressures than the +/− 6 mm Hg.

Reading of volume change in the bellows is accomplished with a voltage divider network, an operational amplifier, a digital voltmeter and a recorder. The linear motion potentiometer is attached to the bellows in such a manner that as the bellows moves, a resistance change takes place and feeds a signal voltage to the operational amplifier. The rate of respiration is taken directly from the pressure readout by recorder trace.

Analyzers are used to detect oxygen and carbon dioxide levels in the system. Oxygen concentration and alarm monitor for high/low levels are provided by a polarographic cell exposed to the gas passing between the bellows and the Barlyme container. A portion of the gas is diverted from the exit side of the Barlyme container through an Infrared Analyzer sensitized for carbon dioxide and returned to the bellows for monitoring carbon dioxide levels. $\Delta P$ and $\Delta V$ are recorded on strip chart recorders as well as the amount of oxygen added.

In addition, the system of this invention can be used as a respiratory simulator by replacing the signal input from the pressure transducer with either a function generator or tape signal.

Clearly evident is the fact that the constant volume rebreathing system of this invention offers a solution to a problem in science that has been under study for over 100 years. In fact with this invention it is now possible to identify over 70 compounds in the expired air of man. This represents a substantial advancement in the knowledge of man's respiratory functions.

It is therefore an object of this invention to provide a rebreathing system which obtains a constant volume when the human lung/diaphragm is incorporated therein.

It is a further object of this invention to provide a rebreathing system which is capable of reliably collecting non-contaminated expired air samples.

It is a further object of this invention to provide a rebreathing system which eliminates the use of diffusable barriers in the system.

It is still a further object of this invention to provide a rebreathing system which reduces the fatigue of the subject using the system.

It is still another object of this invention to provide a rebreathing system which is economical to produce and which utilizes conventional, currently available components that lend themselves to standard mass producing manufacturing techniques.

For a better understanding of the present invention together with other and further objects thereof reference is made to the following description taken in connection with the accompanying drawing and its scope will be pointed out in the appended claims.

DESCRIPTION OF THE PREFERRED EMBODIMENT

Figure 1:
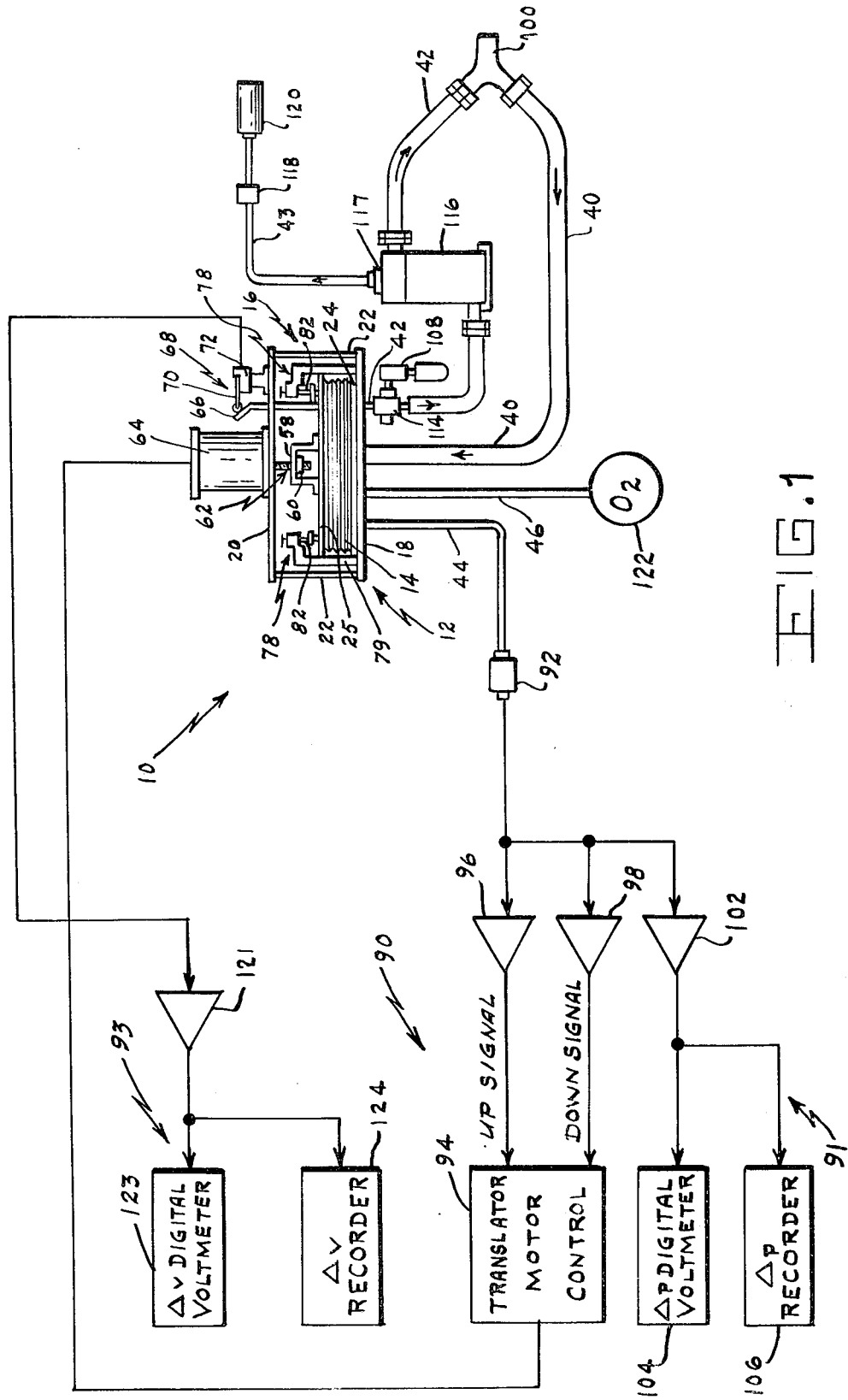
FIG. 1 is a schematic representation of the rebreathing system of this invention.
Figure 2:
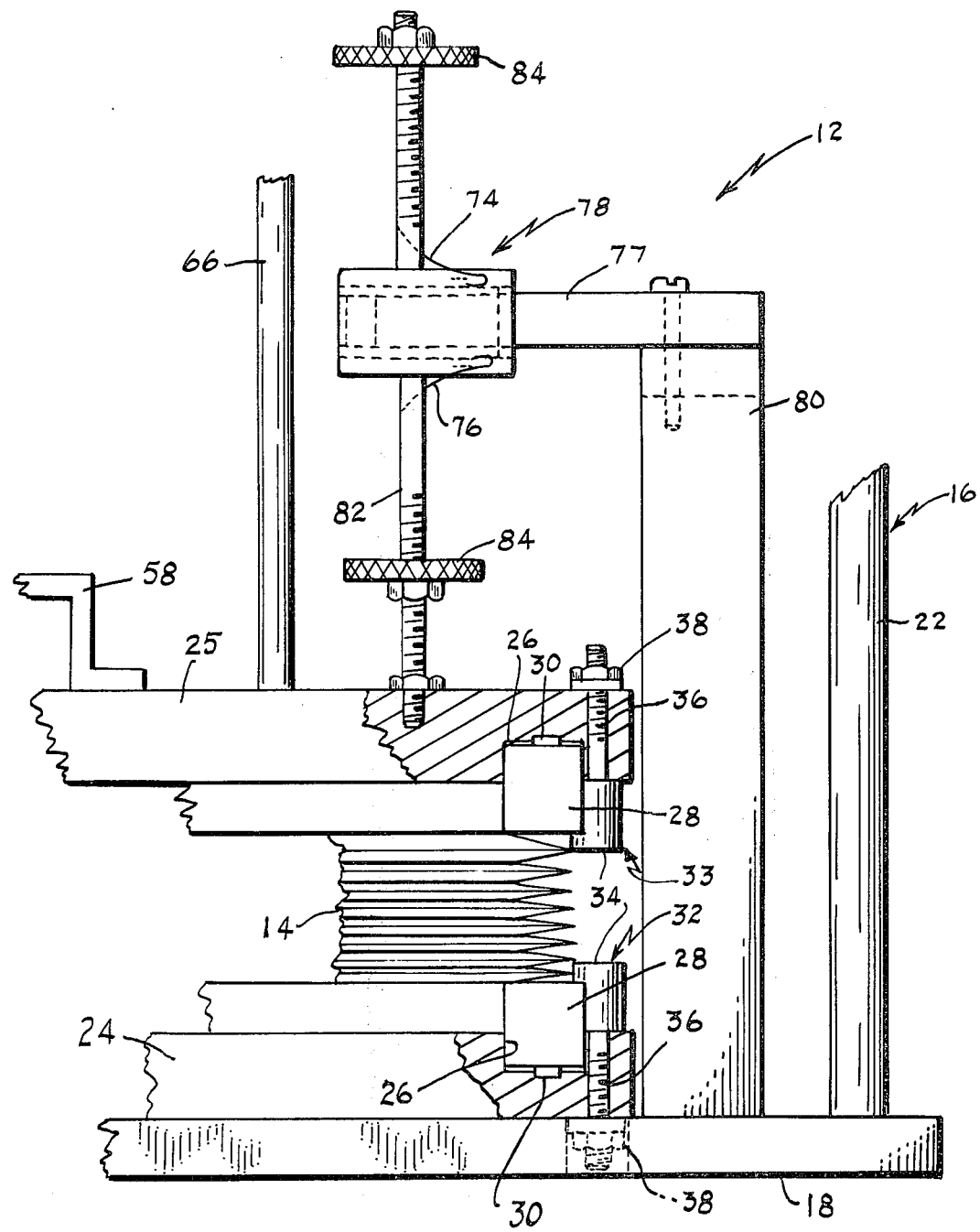
FIG. 2 is a detailed side elevational view of the bellows portion of the rebreathing system of this invention shown partly in cross-section.

Reference is now made to FIGS. 1 and 2 of the drawing which best show the rebreathing system 10 of this invention. Forming a major component of system 10 is bellows portion 12. Bellows portion 12 incorporates therein a bellows 14, a frame 16 which supports bellows 14, and the mechanical and electrical equipment (described in detail hereinbelow) that govern its operation.

Supporting frame 16 is formed of a pair of plates 18 and 20, preferably manufactured of stainless steel, mounted in spaced relationship with respect to one another by means of a plurality of upstanding rods 22. Mounted within frame 16 is bellows 14 made of any suitable material such as stainless steel. Enclosing bellows 14 and forming the top and bottom thereof are a pair of plates 24 and 25. Each plate 24 and 25 contain on one surface a wide groove 26 about the circumference thereof as clearly shown in FIG. 2. Grooves 26 are so designed to accept a pair of square cut rings 28 provided as an integral part of stainless steel bellows 14. Also located within each groove 26 is a gasket 30 preferably of silicone rubber to provide a seal between bellows 14 and plates 24 and 25.

In order to secure bellows 14 to plates 24 and 25, respectively, any suitable pair of removable clamping arrangements 32 and 33, as clearly shown in FIG. 2, can be utilized. Clamping arrangements 32 and 33 are each formed of an L-shaped element 34, the lip of which engages the exposed portion of ring 28 with a fastening element 36 secured within each plate 24 and 25 by any suitable removable fastening means such as nut 38. With such a clamping arrangement 32, 33 it is possible by the loosening of nut 38 and subsequent rotating of element 34 to remove bellows 14 for cleaning or replacement without the removal of either plates 24 and 25 or clamping arrangements 32 and 33.

Referring once again to FIGS. 1 and 2, plate 24 is securely mounted upon base plate 18 by any conventional securing means while plate 25 is freely moveable within frame 16. In addition base plate 18 is furnished with orifices for connection of an expired air hose 40, an inspired air hose 42, a pressure transducer line 44, an oxygen supply line 46, and any additional measuring devices to be added at a later time.

Reference is again directed to FIG. 2 of the drawing, and in particular, to plate 25 which provides on the upper surface thereof mounting for a bracket 58 for a recirculating ball nut 60 of a conventional saginaw ball screw drive 62 which is utilized in conjunction with any conventional stepping drive motor 64 mounted upon upper plate 20. In addition to the mounting of bracket 58 on plate 25, plate 25 also mounts thereon a brass rod 66 utilized in conjunction with a volume measuring system 68 (shown in FIG. 1) mounted upon plate 20. Rod 66 is bent, preferably at a 30 degree angle, at the top portion thereof thereby remaining in engaging relationship with a slideable rod 70 of a linear potentiometer 72 of volume measuring system 68.

In order to preclude the possibility of injury to the subject using the instant invention or to the equipment, a pair of duplicate limit switches 74 and 76 form part of a safety arrangement 78. Limit switches 74 and 76 are mounted on an extension 77 on each of a pair of posts 79 and 80, respectively. A rod 82 is slidably mounted within each extension 77 adjacent limit switches 74 and 76. Plate 25 is fixedly secured to one end of each rod 82 while a pair of adjustable circular nuts 84, defining the upper and lower limits of the movement of bellows 14, are adjustably mounted on rod 82, one such nut 84 being located intermediate plate 25 and extension 77 while the other nut 84 is located at the other end of rod 82. These nuts 84 contact switches 74 and 76 and control the activation or deactivation of the rebreathing apparatus of this invention in a manner to be described in more detail hereinbelow.

Bellows 14 is connected to several ancillary systems in order to obtain the constant volume rebreathing system 10 when utilized in conjunction with a subject. As shown in FIG. 1 the volume of system 10 is controlled by means of the movement of bellows 14. In order to accomplish the volume control, a translator control circuit 90 is actuated by a pressure transducer 92 operably connected to transducer line 44. Transducer 92 controls any suitable motor translator 94 such as a Superior-Electric HTR-1500 translator in a manner to be described hereinbelow. Motor 64 is electrically connected to translator 94 while being mechanically linked to bellows plate 25 by ball screw drive 62 as described hereinabove. This arrangement opens and closes bellows 14.

Figure 4:
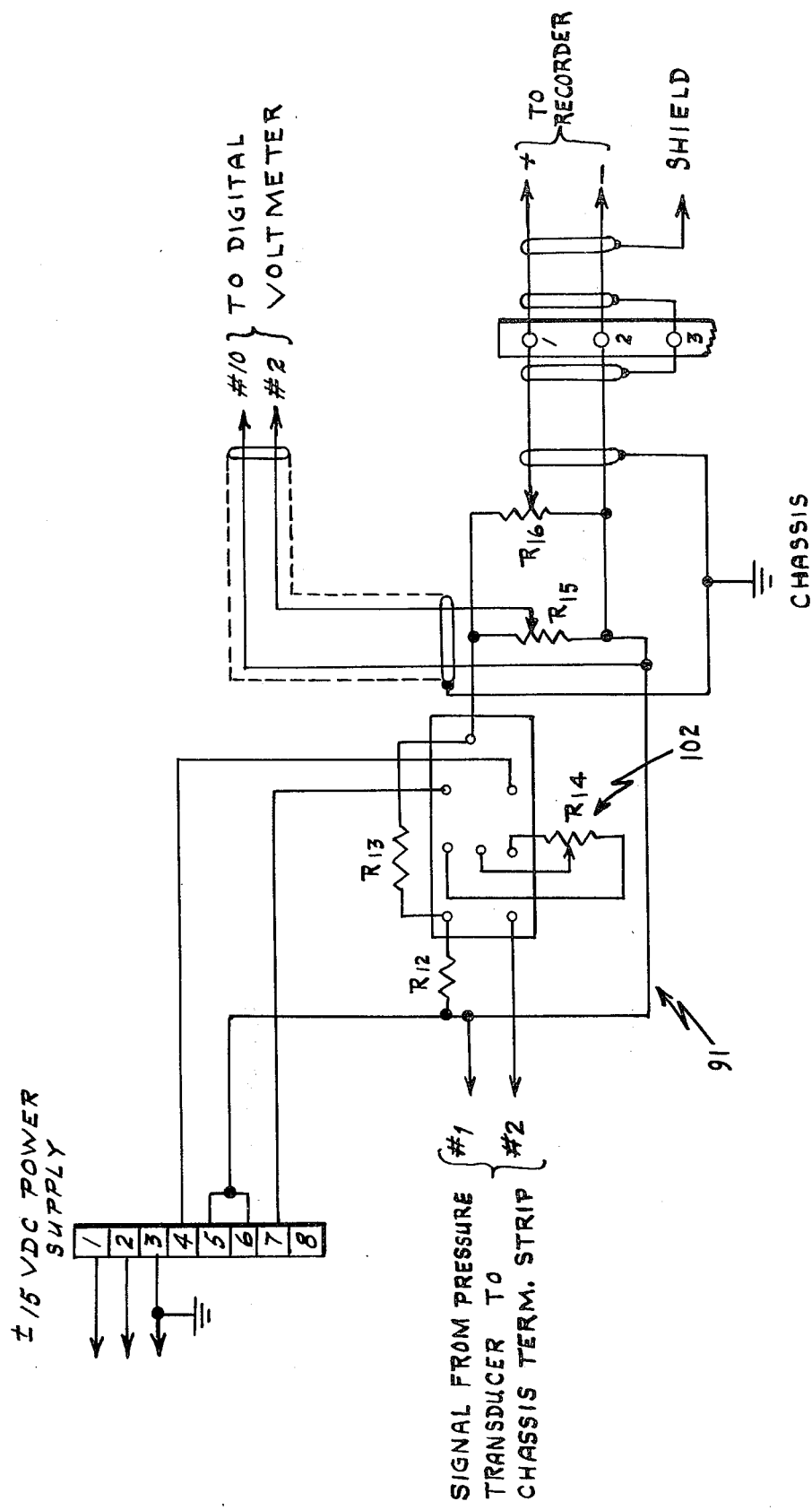
FIG. 4 is a schematic diagram of the ΔP circuit forming a part of the rebreathing system of this invention.

The signal from pressure transducer 92 is passed through a conditioning network shown in detail in FIG. 4. This network is made up of up and down amplifiers 96 and 98, respectively, which are electrically connected between transducer 92 and translator 94. In operation pressure transducer 92 through line 44 senses the bellows and ambient differential pressure between bellows 14 and the lung of a subject breathing through valve 100 of system 10. This differential pressure signal is fed by transducer 92 to amplifiers 96 and 98, from there to translator 94 and in turn to motor 64. Motor 64 will then operate to equalize pressure. Such action causes bellows 14 to follow the subject's breathing pattern. The ΔP output from amplifier 102 is displayed on a digital voltmeter 104 and a strip chart recorder 106.

A two-way valve 100, operably connected to an expired air line 40 and inspired air line 42, is utilized in controlling the direction of air flow from the subject. The expired air of the subject is directed to bellows 14 by line 40. When inspiration begins, the expired air side of valve 100 seals, and the inspired side of valve 100 opens allowing air to enter through line 42.

In other words, the rebreathing system 10 of this invention controls the differential pressure between a subject's lungs and the stainless steel bellows 14. As the subject inspires, pressure transducer 92 senses the pressure change, and presents the signal through control amplifiers 96 and 98 to translator 94 which drives the motor control for bellows 14 and compresses the volume of bellows 14. Conversely, as the subject expires, motor 64 expands the volume of bellows 14. Therefore, a constant volume is maintained between the subject's lung and rebreathing system 10 of this invention. For example, a differential pressure of ± 2 mm Hg during normal respiration is produced by system 10.

Also incorporated within rebreathing system 10 of this invention is a solenoid operated over-pressure or relief valve 108. At a predetermined pressure, such as 6 mm Hg, valve 108 opens bellows 14 to the ambient atmosphere thereby providing protection to the subject in the event of a system malfunction producing a lower or higher pressure than the predetermined pressure.

Stream analyzers are used with this invention to detect the oxygen and carbon dioxide levels in system 10. Oxygen is monitored with any suitable conventional oxygen analyzer 114 such as manufactured by International Biophysics Corporation as Model 145M Oxygen Analyzer. Analyzer 114 is located adjacent relief valve 108 in line 42. This instrument 114 is capable of measurement ranges of 0–250 and 0–1000 mm. Hg oxygen partial pressure. The accuracy of analyzer 114 is better than ± 2 percent of a reading for 24 hours at a constant temperature and humidity. Oxygen in the sample gas is diffused through a membrane of a polarographic cell and electrochemically reduced at the cathode of the sensor's cathode-anode cell. This causes a current to flow between the elements. Located adjacent oxygen analyzer 114 in line 42 is a baralyme canister 116. A portion of the gas is diverted from the exit side 117 of baralyme canister 116 by line 43 through any suitable pump 118 to any suitable conventional Infrared Analyzer 120 sensitized for carbon dioxide such as Beckman Model 315 and then returned to the system. Analyzer 120 is calibrated for carbon dioxide with 10 percent gas providing a full scale reading. Oxygen is added to system 10 automatically through line 46 from source 122 by means of a circuit driven by the recorder output of the oxygen analyzer 114 and a motor servo-system (not shown).

Reading of the volume change within bellows 14 is accomplished with operational amplifier 121, a digital voltmeter 123, and a recorder 124. A linear motion potentiometer 72 is attached to bellows 14 in such a manner that as the bellows 14 moves, a resistance change takes place in potentiometer 72 and feeds a signal voltage to the operational amplifier 121. The signal conditioned by amplifier 121 is presented on a digital voltmeter 123 and strip chart recorder 124.

Figure 3:
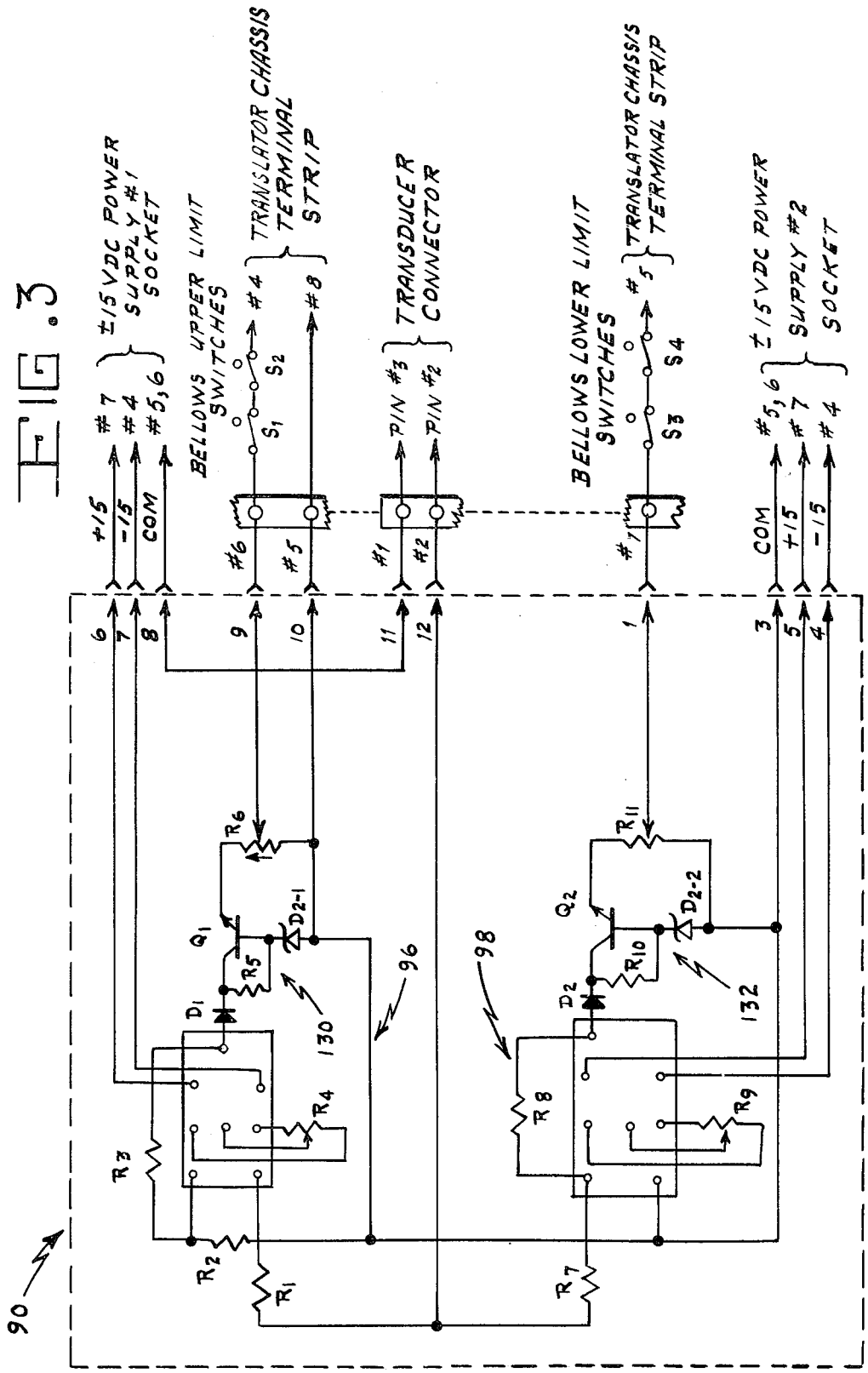
FIG. 3 is a schematic diagram of the translator control circuit forming a part of the rebreathing system of this invention.
Figure 5:
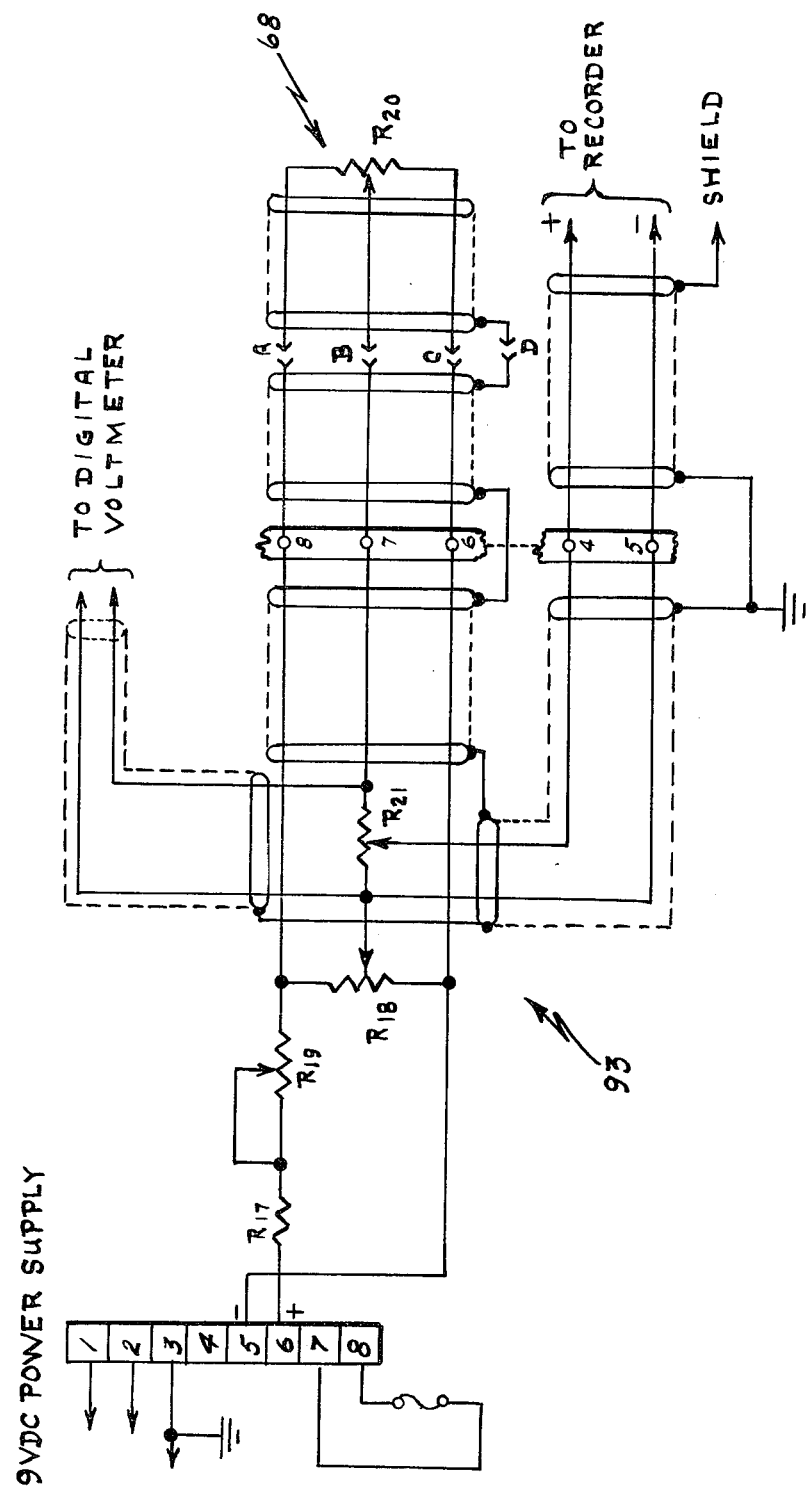
FIG. 5 is a schematic diagram of the ΔV circuit forming a part of the rebreathing system of this invention.

Reference is now made to FIGS. 3–5 which show in schematic fashion the main electrical circuits which make up the rebreathing system 10 of this invention. In particular FIG. 3 represents the translator control circuit 90 which contains therein up Amplifier 96 and down Amplifier 98. An example of amplifiers 96 and 98 may be Burr-Brown Model 3004 operational amplifiers.

First we shall consider the operation of up drive Amplifier 96 connected as a non-inverting circuit and described as follows:

a. Resistor $R_1$ on amplifier 96 is the compliment of resistor $R_7$ on amplifier 98. These are the input voltage divider resistors for the signal from pressure transducer 92.

b. Resistors $R_2$ and $R_3$ form the feedback network and establish the gain for circuit 90. Resistor $R_4$ is used as a zero offset control.

c. $D_1$ is a signal diode used such that transistor $Q_1$ will not allow a negative signal.

d. Transistor $Q_1$, resistor $R_5$ and diode $D_{2-1}$ make up the regulator circuit 130 which is used to regulate the output drive signal to translator 94.

e. A potentiometer $R_6$ preferably of 10K ohms is used to control the amount of output signal to translator 94. This in turn controls the speed of drive motor 64 in an upward direction.

f. There are two limit switches located on bellows 14. These switches 76 are connected in series to the output signal line to translator 94. They establish the upper limit of travel for bellows 14.

Next we will consider the operation of down drive Amplifier 98 connected as an inverting circuit as follows:

a. Resistor $R_7$ is the compliment of resistor $R_1$ on amplifier 96. These are the input voltage divider resistors for the signal from pressure transducer 92.

b. Resistor $R_7$ is also part of the feedback gain circuit with resistor $R_8$. Resistor $R_9$ is used as a zero offset control.

c. $D_2$ is a signal diode connected to transistor $Q_2$ to prevent negative signal swing.

d. Transistor $Q_2$, resistor $R_{10}$ and diode $D_{2-2}$ make up the regulator circuit 132 which regulates the output drive signal to translator 94.

e. A potentiometer $R_{11}$ preferably of 10K ohms controls the amount of output signal to translator 94. This in turn controls the speed of drive motor 64 in a downward direction.

f. There are two limit switches 74 located on bellows 14. These switches 74 are connected in series with the output signal to translator 94. They set the lower limit of travel for bellows 14.

Still referring to FIG. 3 a signal from transducer 92 is fed to translator circuit 90. Output from circuit 90 is connected to translator 94 which furnishes a drive signal to motor 64 controlling the bellows position. Switches S1, S2, S3, and S4 are the signal limit switches. They will cut signal to translator 94 and stop the drive of motor 64 should bellows 14 attempt to drive past the set limits. Any conventional backup switches (not shown) serve as a backup to the signal limit switches and will turn off translator 94 if bellows 14 goes beyond the set limits.

Reference is now made to FIG. 4 which best shows the $\Delta P$ circuit 91 which uses a $\pm 15$ vdc power supply. Circuit 91 utilizes a non-inverting amplifier 102. A signal is fed to amplifier 102 from pressure transducer 92. This circuit isolates the signal from transducer 92 and provides the necessary gain to the readouts. Resistors $R_{12}$ and $R_{13}$ form the feedback network and establish gain for circuit 91. Resistor $R_{14}$ is used as a zero offset control. Resistor 15 is the span control for the readout from digital voltmeter 104 and resistor $R_{16}$ is the span control for the readout from recorder 106.

Reference is now made to FIG. 5 which best shows the $\Delta V$ circuit 93. Circuit 93 is a simple voltage divider network using a 9vdc as a voltage source. Within circuit 93 resistors $R_{17}$ and $R_{19}$ control the amount of voltage to the network. Resistor $R_{19}$ serves as a span control. Resistors $R_{18}$ and $R_{20}$ make up the signal divider network. Resistor $R_{20}$ is the Linear Motion potentiometer 68 which varies as bellows 14 moves up and down. Resistor $R_{18}$ is used to zero the output signal at any desired position of bellows 14. The signal amplitude is controlled by resistor $R_{19}$ and displayed on digital voltmeter 122. The signal amplitude of strip chart recorder 124 is controlled by resistor $R_{21}$.

As clearly shown hereinabove the rebreathing system 10 of the instant invention provides a completely closed breathing system isolating man from the external environment. The incorporation of a flexible metal bellows 14 eliminates the diffusable barriers found in other systems, such as polymeric organic materials and water; thereby, eliminating gaseous diffusion. Pressure transducer 92 is used to drive a stepping motor 64 incorporated as a servo-system amplifying the action of the subject's respiratory effort in a man machine interface. Hence, this invention presents master-slave type relationship which is completely reliable and efficient in operation.

Although this invention has been described with reference to a particular embodiment it will be understood to those skilled in the art that this invention is also capable of a variety of alternate embodiments within the spirit and scope of the appended claims.

We claim:

1. A rebreathing system comprising a supporting structure, a container having a variable volume mounted within said structure, a pair of conduits operably connected to said container and adapted to be connected to a person for allowing air to enter and escape from said container, means operably connected to said conduits for controlling the flow of air therethrough, means operably connected to said container for sensing a pressure change within said container and providing a signal in accordance therewith, means operably connected to said container for varying the volume thereof, means operably connected between said pressure change sensing means and said volume varying means for transmitting said signal to said volume varying means to control said volume varying means in accordance with said signal, a rod fixedly secured to said container, said rod having one portion thereof inclined at an angle, a potentiometer mounted on said supporting structure, said potentiometer having a slideable element, said slideable element being in engaging relationship with said inclined portion of said rod whereby a volumetric change of said container causes movement of said slideable element thereby causing said potentiometer to emit a signal in accordance with said volumetric change, means for recording said volume change signal, means operably connected to said bellows for detecting a preselected volume change therein and emitting a signal in accordance therewith, said preselected volume detecting means being operably connected to said transmitting means for controlling the activation or deactivation of said system whereby a constant volume is maintained between said system and said person.

2. A rebreathing system as defined in claim 1 wherein said container is in the form of a bellows and a pair of end plates, one of said end plates of said bellows being fixedly mounted on said supporting structure, said other end plate of said bellows being moveable within said supporting structure and means removably securing said end plates to said bellows.

3. A rebreathing system as defined in claim 2 further comprising means operably connected to said container for opening said bellows to the atmosphere at a predetermined pressure.

4. A rebreathing system as defined in claim 3 further comprising at least one air analyzer located within one of said conduits.

5. A rebreathing system as defined in claim 4 wherein said means for transmitting said pressure change signal to said volume varying means comprises at least one amplifier and a signal translator.

6. A rebreathing system as defined in claim 5 wherein said volume varying means comprises a stepping motor and a ball screw drive connected to said bellows.

7. A rebreathing system as defined in claim 6 wherein said means for detecting a preselected volumetric change in said bellows comprises at least one rod mounted on said bellows, a pair of nuts adjustably mounted on said rod and a pair of limit switches mounted on said supporting structure and in operable relationship with said pair of nuts.

8. A rebreathing system as defined in claim 7 further comprising an oxygen source operably connected to said bellows.

9. A rebreathing system as defined in claim 8 wherein said pressure change sensing means is a pressure transducer.

10. A rebreathing system as defined in claim 9 further comprising a digital voltmeter operably connected to said pressure transducer.

11. A rebreathing system as defined in claim 10 wherein said means for recording said volume change signal comprises a digital voltmeter operably connected to said potentiometer.

* * * * *